Jan. 20, 1959 E. S. BOERNER Plant Pat. 1,803
ROSE PLANT
Filed June 3, 1958
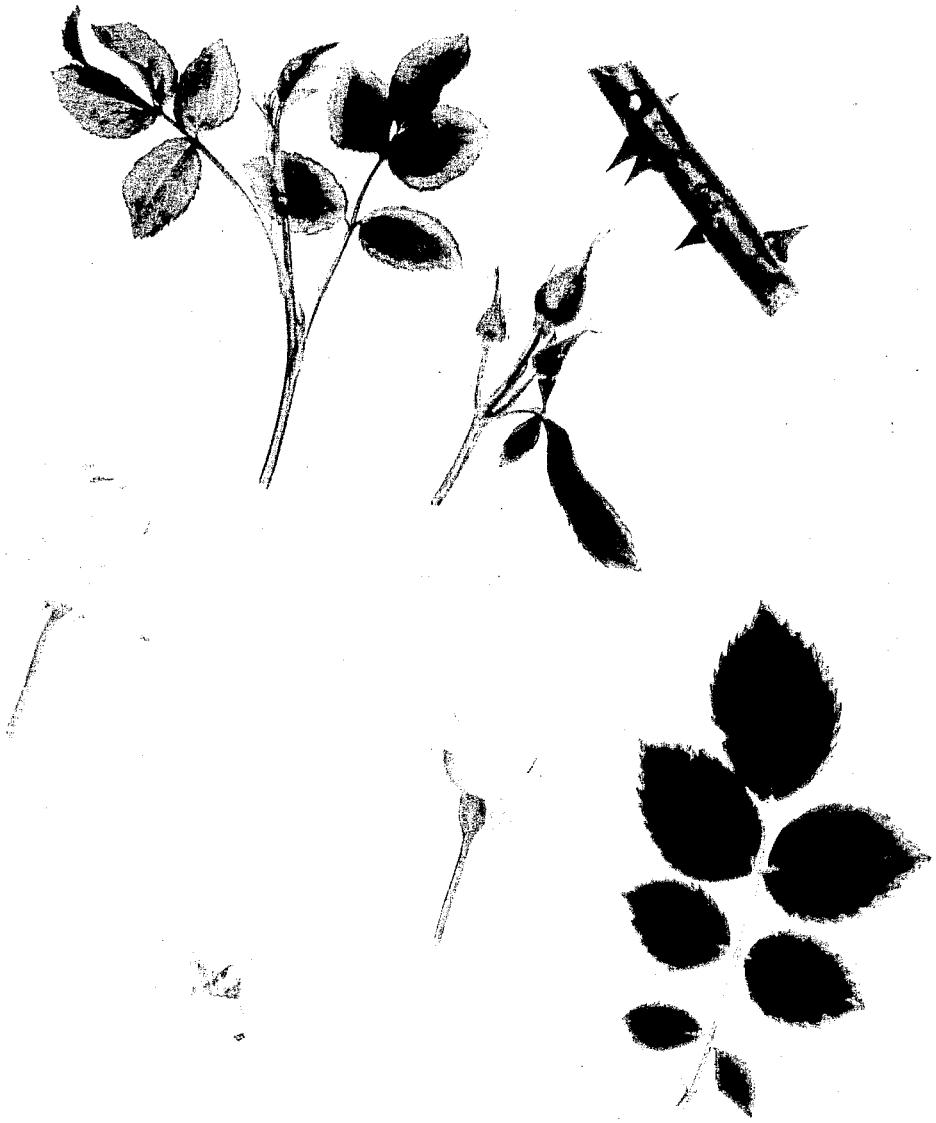
Inventor.
E. S. Boerner
By: Robb & Robb
Attorneys.

United States Patent Office

Plant Pat. 1,803
Patented Jan. 20, 1959

1,803

ROSE PLANT

Eugene S. Boerner, Newark, N. Y., assignor to Jackson & Perkins Company, Newark, N. Y., a corporation of New York Application June 3, 1958, Serial No. 739,643

1 Claim. (Cl. 47—61)

The present invention relates to a new and distinct variety of rose plant of the large-flowered polyantha class, which was originated by me by crossing the variety "Chic" (Plant Patent No. 1,286) with the variety "Demure" (Plant Patent No. 1,065).

The primary objective of this breeding was to produce a new rose variety which combines therein the excellent qualities of both parent varieties, while at the same time achieving long-lasting and good keeping qualities of blooms of other colors. This objective has been fully achieved, as the result of which, the present variety represents a new and distinct variety having a unique combination of characteristics amongst which the following are outstanding:

(1) A great number of leaflets;

(2) Unusually heavy thorns for a rose of this type;

(3) Flowers of a larger size than those of "Demure," but with equally good keeping qualities; and (4) A distinctive Thulite Pink general color tonality of the flowers, lightly overcast with Rose Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Chic."
*Pollen parent.*—"Demure."

Classification:
*Botanic.*—Large-flowered polyantha.
*Commercial.*—Floribunda.

*Flower*

(Observations made from specimens grown in a greenhouse at Newark, New York, near mid-afternoon in the latter part of January.)

Blooming habit: Recurrent—continuous.

Bud:
*Size.*—Medium.
*Form.*—Ovoid; is not affected by wet or hot weather.
*Color.*—When sepals first divide—Thulite Pink, Plate 26. When petals begin to unfurl—Spinel Pink, Plate 26. When half-blown: inside of petals—Thulite Pink, Plate 26, lightly overcast with Spinel Pink, Plate 26; reverse of petals—Cameo Pink, Plate 12.
*Sepals.*—Slightly branched; curl back when petals begin to unfurl. Color: inside—Light Fluorite Green, Plate 32; outside—Chromium Green, Plate 32.
*Calyx.* — Color — Light Bice Green, Plate 17. Shape—funnel. Size—small. Aspect—smooth. Odor when rubbed—none.
*Peduncle.* — Length — medium. Aspect — rough. Strength—erect; slender. Color—Light Bice Green, Plate 17.
*Opening.*—Opens up well; is not affected by adverse weather conditions.

Bloom:
*Size.*—Medium. Average size when fully expanded—2¾ inches.
*Borne.*—Singly and several together and in irregular clusters.
*Stems.*—Medium length; normal strength.
*Form (when first open).*—Cupped and with globular center. Permanence—Flattens.
*Petalage.*—Double (full but open center). Number of petals under normal conditions—from 40 to 45.
*Color.*—Center of flower—Rose Pink, Plate 12, lightly overcast with Thulite Pink, Plate 26. Outer petals—Cameo Pink, Plate 26, lightly overcast with Rose Pink, Plate 12. Base of petals (aiglet)—Sea-Foam Yellow, Plate 31. Inside of petals—Thulite Pink, Plate 26, lightly overcast with Rose Pink, Plate 12. Reverse of petals—Rose Pink, Plate 12.
*General tonality from a distance.*—Thulite Pink, Plate 26, lightly overcast with Rose Pink, Plate 12.
*Discoloration.*—General tonality at end of first day—Rose Pink, Plate 12, lightly overcast with Thulite Pink, Plate 26. Second day—Thulite Pink, Plate 26, lightly overcast with Rose Pink, Plate 12. Third day—Rose Pink, Plate 12.

Petals:
*Texture.*—Leathery; is not affected by wet or hot weather.
*Appearance.*—Inside—satiny. Outside—shiny.
*Form.*—Oval.
*Arrangement.*—Irregular.
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Small; many; regularly arranged around styles. Color—Pale Greenish Yellow, Plate 5.
Stamens, filaments (threads): Short. Color—Pale Chalcedony Yellow, Plate 17.
Pollen: Color—Sulphur Yellow, Plate 5.
Styles: Loosely separated; medium length; thin.
Stigmas: Color—Naples Yellow, Plate 16.
Ovaries: All enclosed in calyx.
Hips: None.
Seeds: None.

*Plant*

Form: Bush.
Growth: Vigorous; upright.
Foliage: Compound of 5—7—9 leaflets.
*Size.*—Medium.
*Quantity.*—Normal.
*Color.*—New foliage: upper side—Madder Brown, Plate 13, with center rib of Courge Green, Plate 17; under side—Victoria Lake, Plate 1. Old foliage: upper side—Forest Green, Plate 17; under side—Light Elm Green, Plate 17.
*Shape.*—Oval.

*Texture.*—Upper side—smooth. Under side—smooth.

*Ribs and veins.*—Ordinary.

*Edge.*—Serrated (saw-toothed).

*Serration.*—Single; small.

*Leaf stem.*—Color—Rainette Green, Plate 31, lightly overcast with Begonia Rose, Plate 1. Under side—prickly.

*Stipules.*—Short; smooth.

Wood:

*New Wood.*—Color—Rainette Green, Plate 31. Bark—smooth.

*Old wood.*—Color—Bice Green, Plate 17. Bark—smooth.

Thorns:

*Thorns.*—Quantity: on main stalks from base—ordinary; on laterals from stalk—ordinary. Form—flat base; heavy; medium length; straight. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of a great number of leaflets, unusually heavy thorns, flowers of a larger size than those of "Demure" (Plant Patent No. 1,065) but having equally good keeping qualities, and a distinctive Thulite Pink general color tonality of the flowers, lightly overcast with Rose Pink.

No references cited.